United States Patent
White, Sr.

[11] Patent Number: 6,053,580
[45] Date of Patent: *Apr. 25, 2000

[54] PERSONAL RESTRAINT DEVICE

[76] Inventor: William E. White, Sr., 6300 Old York Rd. Apt. 1316, Philadelphia, Pa. 19141

[*] Notice: This patent issued on a continued prosecution application filed under 37 CFR 1.53(d), and is subject to the twenty year patent term provisions of 35 U.S.C. 154(a)(2).

[21] Appl. No.: 09/177,147

[22] Filed: Oct. 22, 1998

[51] Int. Cl.[7] .................................................. A47C 31/00
[52] U.S. Cl. ......................... 297/467; 297/485; 297/486
[58] Field of Search .................... 297/464, 467, 297/485, 486, 487, 465, 488

[56] References Cited

U.S. PATENT DOCUMENTS

| | | |
|---|---|---|
| 2,451,007 | 10/1948 | White . |
| 3,529,864 | 9/1970 | Rose et al. . |
| 4,428,514 | 1/1984 | Elf . |
| 4,913,498 | 4/1990 | Forlivio ................................. 297/488 |
| 4,927,211 | 5/1990 | Bolcerek . |
| 5,002,338 | 3/1991 | Gisser .................................. 297/250 |
| 5,042,878 | 8/1991 | Collins . |
| 5,056,869 | 10/1991 | Morrison . |
| 5,286,090 | 2/1994 | Templin et al. ...................... 297/473 |
| 5,299,855 | 4/1994 | Zubeck ................................. 297/485 |
| 5,449,216 | 9/1995 | Gierman et al. ................. 297/216.11 |
| 5,536,066 | 7/1996 | Sedlack .............................. 297/250.1 |
| 5,540,239 | 7/1996 | McClellan ............................. 128/869 |
| 5,713,630 | 2/1998 | Kvalvik . |

OTHER PUBLICATIONS

School Bus Parts Co. Catalog (title unknown); Restraint Systems; ©1990 School Bus Parts Co.; p. 127.

*Primary Examiner*—Milton Nelson, Jr.
*Attorney, Agent, or Firm*—Volpe and Koenig, P.C.

[57] ABSTRACT

The present apparatus is a personal restraint device for fully restraining the wearer while providing flexibility and limited movement during use. The personal restraint device of this invention comprises a harness with a central portion having spaced apart top, bottom and lateral edges that define the parameter of the central portion and portion for securing the personal restraint device to an existing seat.

6 Claims, 8 Drawing Sheets

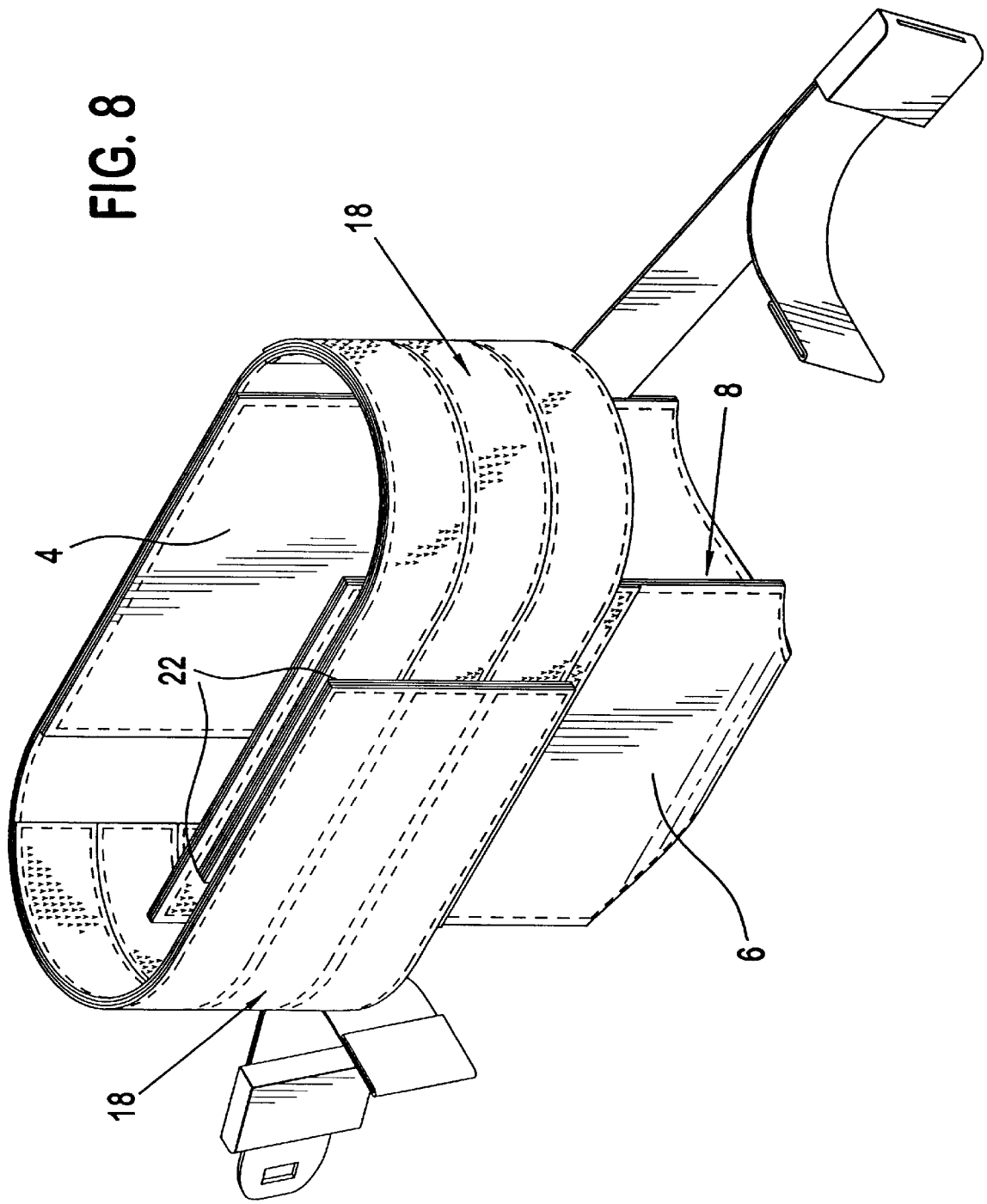

PERSONAL RESTRAINT DEVICE

BACKGROUND OF THE INVENTION

1. Field of the Invention

This invention generally relates to a harness-like personal restraint device. More particularly, the invention relates to a personal restraint device for safely restraining a person in a stationary chair, wheelchair or vehicle, who is either physically challenged or of a size or weight too large for a child's car seat and too small or frail to be safely restrained using adult seatbelt restraints.

2. Description of the Prior Art

Various types of personal restraining devices are well known in the art. U.S. Pat. No. 5,540,239 is an example of a general personal restraint device for use with a chair, shopping cart, highchair, stroller, carriage, wheelchair, or the like. It has multiple straps adapted to cross the body of the restrained person. This device has straps to restrain the wearer's waist, chest, head, and legs against movement away from the seat back. This restraint uses hook and pile fasteners to secure the free end of each strap after attachment to an existing seat.

U.S. Pat. No. 5,286,090 is an example of a basic child car seat with integrally connected back and seat portions.

U.S. Pat. No. 5,299,855 teaches a booster seat for use in an adult seat during transportation. The booster has straps which are inserted between the lower and back portions and over the back portion of the existing seat, and connected by a buckle to the top surface of the back.

U.S. Pat. No. 5,002,338 discloses a support with a harness for securing a child to a person's lap or the back of a vehicular seat.

U.S. Pat. No. 4,913,498 discloses a child restraining device incorporated into the back of an automobile seat. One embodiment of this invention includes straps that cross in front of the child in an X-form to provide additional restraint.

U.S. Pat. No. 5,449,216 discloses a two-occupant bench type passenger seat having a pair of child restraint seats integrated into its underlying frame structure.

U.S. Pat. No. 5,536,066 discloses a device for securing an automotive child restraint or baby seat onto a bench type seat.

Virtually all automotive passenger type motor vehicles are equipped with safety belt restraint systems for physically restraining the seated occupant. Such conventional safety belt restraint systems are lap belts and child restraint seats.

However, there exists a need to provide a personal restraint device, designed to provide protection during sudden movements, such as a collision or sudden stop, that is easily used, transportable and flexible enough to allow limited movement of the wearer, while safely restraining wearers of various sizes and physical conditions.

While the present invention is described in association with a seating arrangement typically recognized as a school bus, it is intended for use with other seating arrangements.

SUMMARY OF THE INVENTION

The present invention is a personal restraint device for fully restraining the wearer while providing flexibility and limited movement during use. The personal restraint device of this invention comprises a longitudinal, generally planar body having back and front portions separated by a connector portion. The front and back portions have generally linear lateral edges and the connector portion has concave edges. The top and bottom transverse edges of the planar body are generally linear. Means for securing the personal restraint device to an existing seat is also provided.

BRIEF DESCRIPTION OF THE DRAWINGS

The present invention will be described with reference to the accompanying drawings in which:

FIG. 8 is a perspective view of the embodiment of FIG. 7 fully assembled.

DETAILED DESCRIPTION OF THE PREFERRED EMBODIMENTS

The preferred embodiments of the invention will be best understood by reference to the drawings, wherein like elements are designated by like numerals throughout.

Figure 1:
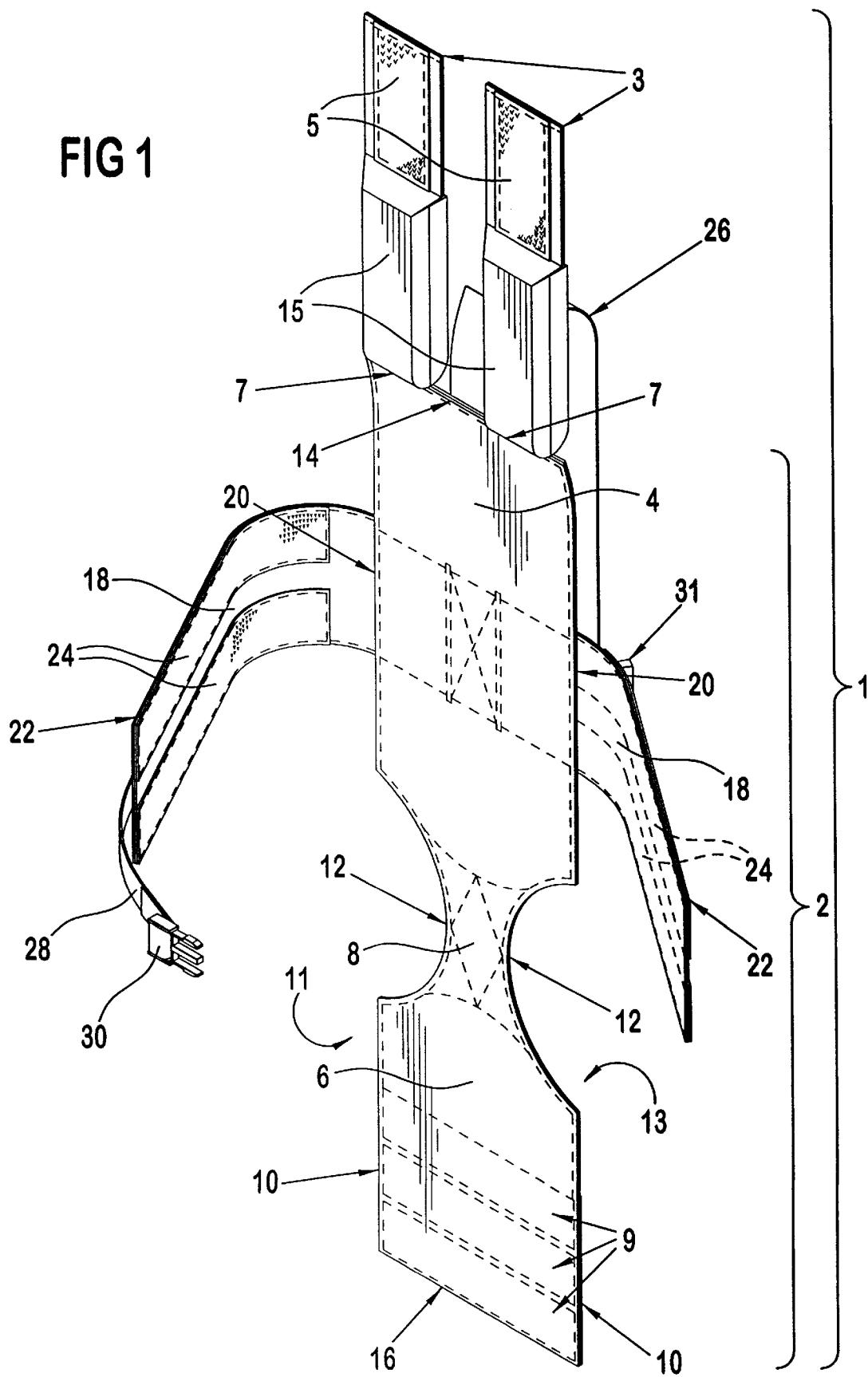
FIG. 1 is a perspective view of a personal restraint device in accordance with the present invention.

With reference to FIG. 1, the personal restraint device 1 has a planar body 2 with inside 11 and outside 13 portions. The back 4 and front 6 portions are separated by the connector portion 8. The back and front portions, 4 and 6, have generally linear edges 10 and the connector portion 8 has concave edges 12. The top and bottom transverse edges, 14 and 16, of the planar body 2 are generally linear. Each of the elongated straps 15 having an end 7 connected to the top transverse edge 14 and a free end 3. The free end 3 of each strap 15 has an element of a detachable fastening means 5 connected thereto. A second, complementary detachable fastening means 9 is attached to the front portion 6. The back portion 4 has at least two horizontal panels 18, each panel 18 having an end 20 connected to the back portion 4 of the planar body 2. Each horizontal strap 18 has a free end 22 which includes a detachable fastening means 24 either on the inside or outside, 11 and 13, of the horizontal panels 18 for securing the free ends 22 of the horizontal panels 18 to the front portion 6 of the planar body 2.

Figure 2:
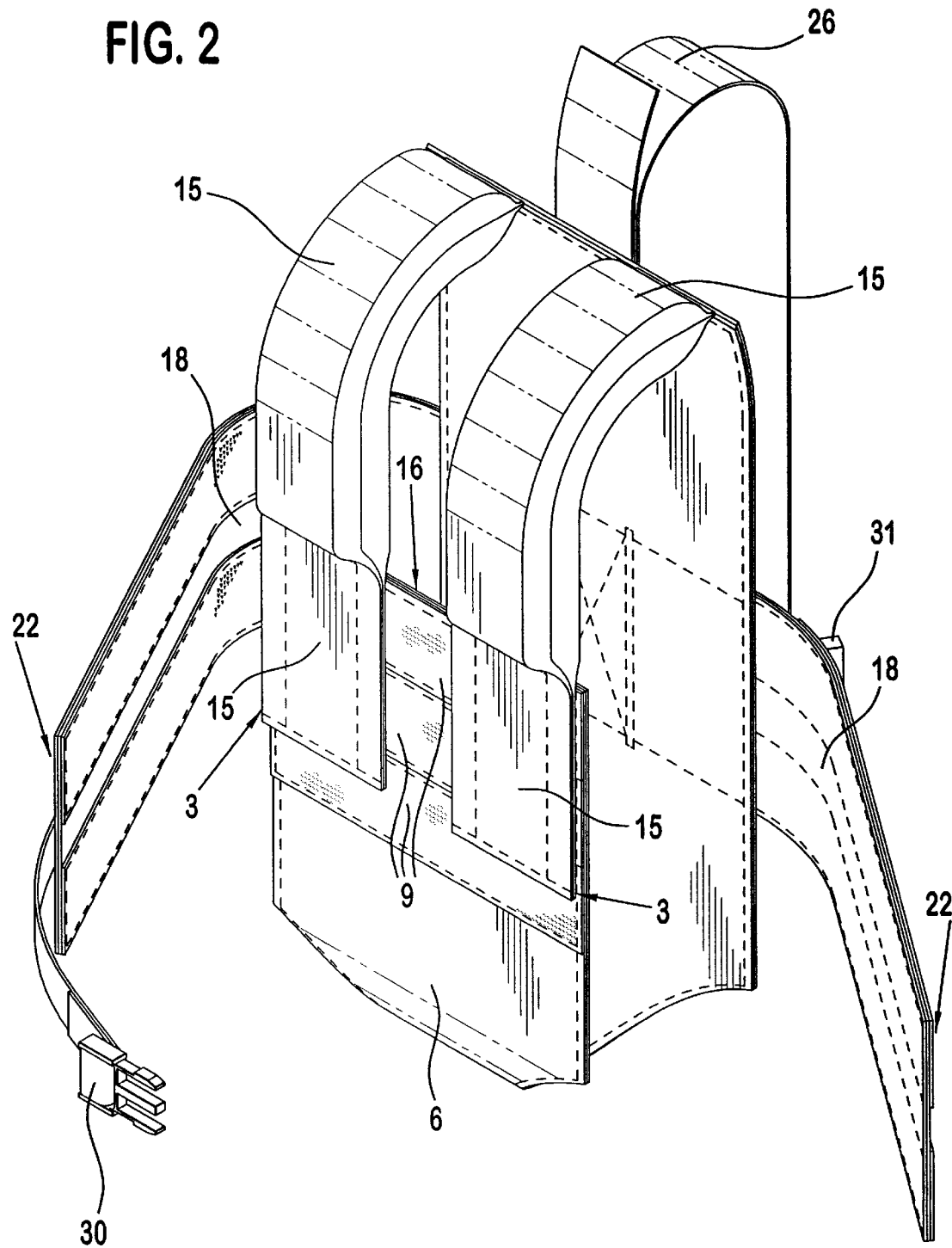
FIG. 2 is a perspective view of the device in FIG. 1 partially assembled.

FIG. 2 illustrates the complementary detachable fastening means 9 attached to the bottom transverse edge 16 of the front portion 6 engaged with the detachable fastening means 5 of the free ends 3 of the elongated straps 15 when the bottom transverse edge 16 of the front portion 6 is brought into proximity to the panels 15. The free ends 22 of the horizontal straps 18 shown in FIG. 2 are not connected.

Examples of detachable fastening means would be a Velcro® type hook and pile fastener, a snap, or a zipper. As illustrated in FIGS. 1 through 6, the back portion 4 of the personal restraint device has means 26 for securing the personal restraint device to an existing seat.

Figure 3:
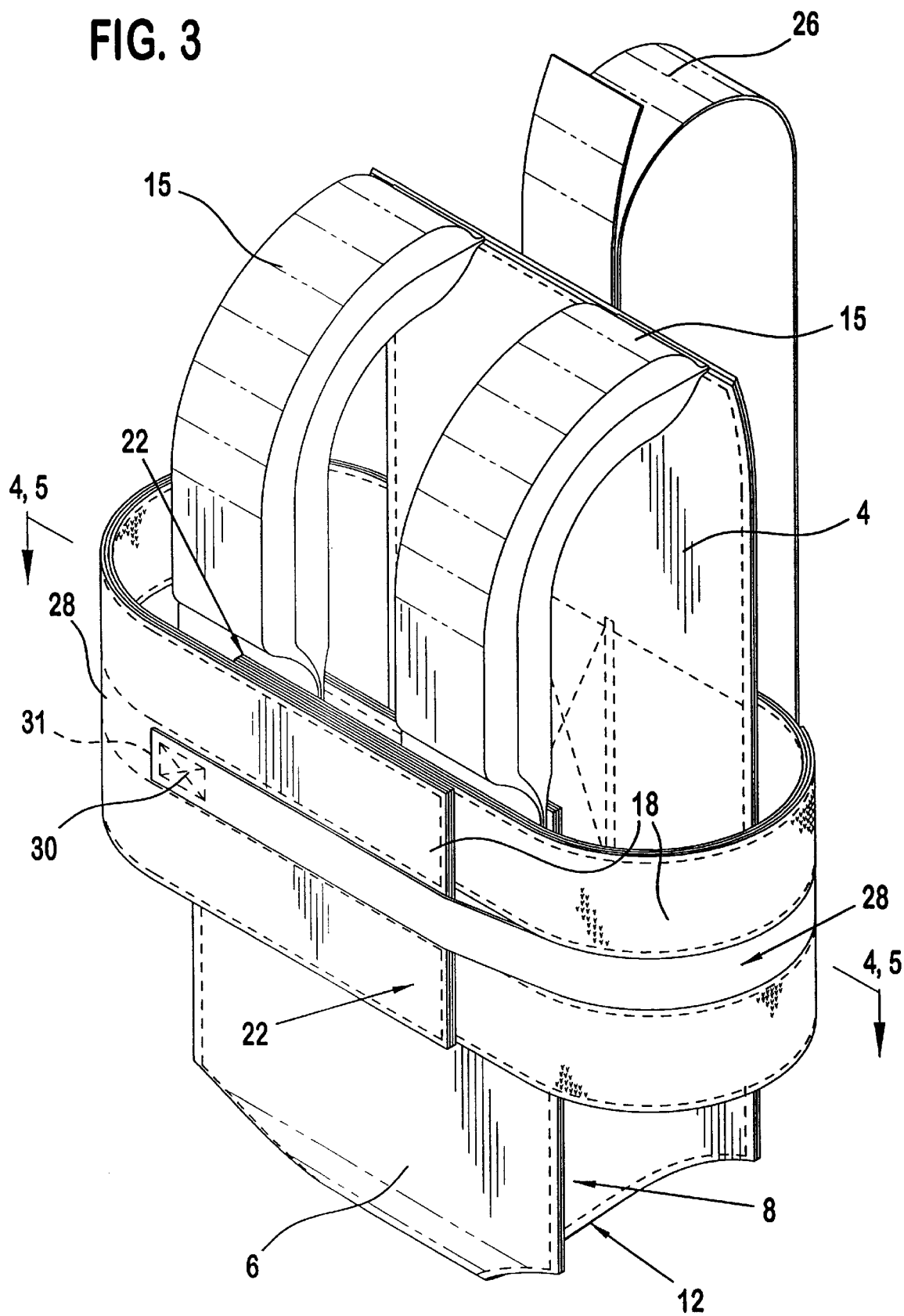
FIG. 3 is a perspective view of the device of FIG. 1 fully assembled.

In addition to what is illustrated by FIG. 2, FIG. 3 further illustrates the horizontal panels 18 connected together, and optionally connected (See FIGS. 4 and 5) to the elongated straps 15 and the front portion 6 of the planar body 2. FIG.

3 illustrates complete assembly of the personal restraint device 1, whereby a person to be restrained can be seated on the connector portion 8 facing away from the back portion 4 and the front portion 6 is brought up against the person's body so that the front portion 6 is opposite the back portion 4 and the free ends 22 of the horizontal panels 18 are secured to each other and optionally to the front portion 6.

Figure 4:
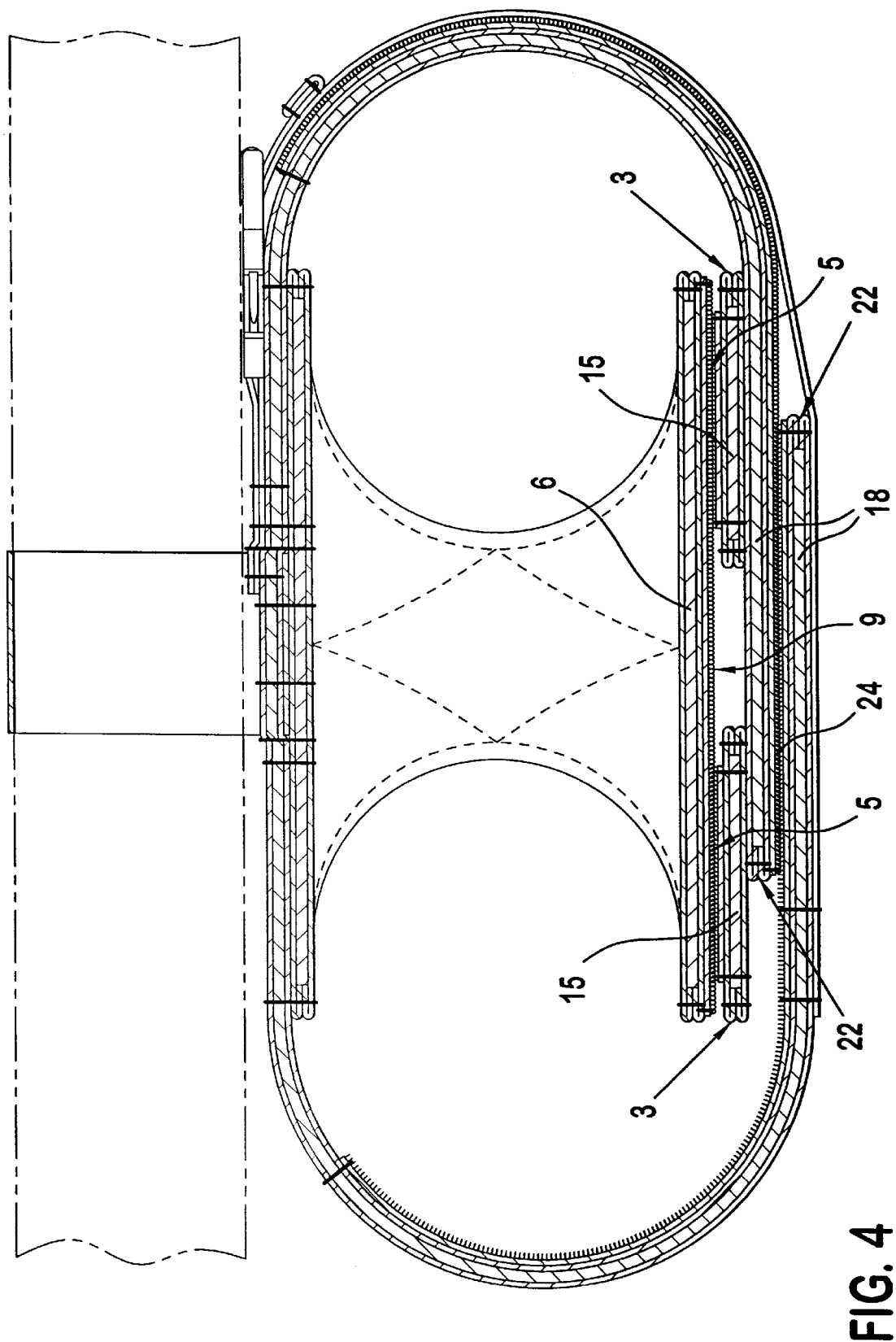
FIGS. 4 and 5 are cross-sections taken along the line 4—4, 5—5 of FIG. 3.
Figure 5:
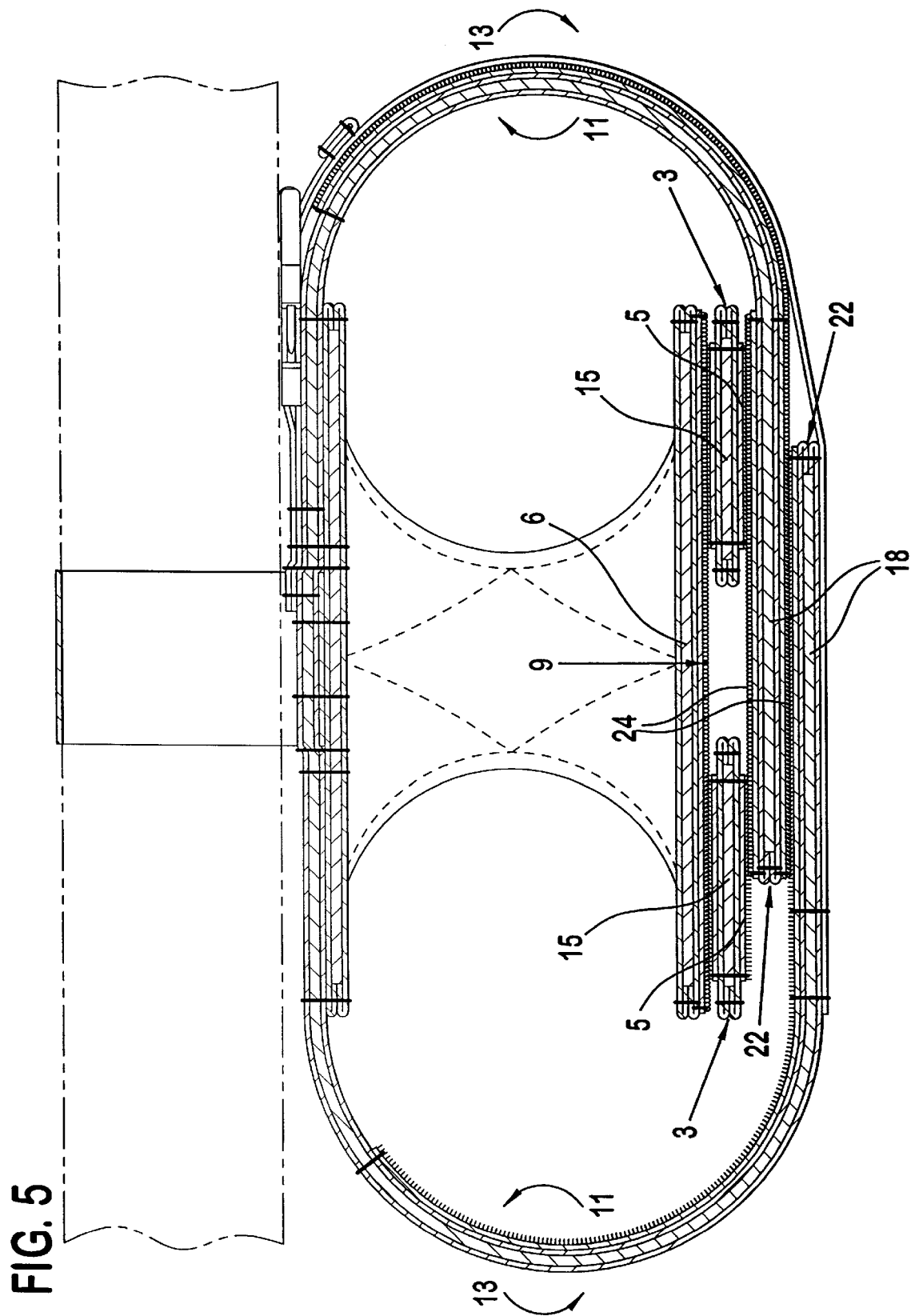

FIGS. 4 and 5 are cross-sectional views of preferred embodiments of the personal restraint device taken along the line 4—4, 5—5 of FIG. 3. Both FIGS. 4 and 5 illustrate the detachable fastening means 5 of the free ends 3 of the elongated straps 15 connected to the complementary detachable fastening means 9 attached to the front portion 6. FIGS. 4 and 5 also illustrate the free ends 22 of the horizontal straps 18 connected to each other by the detachable fastening means 24 of the horizontal panels 18. FIG. 5 illustrates a horizontal panel 18 having the detachable fastening means 24 on both the inside 11 and the outside 13 portions of the horizontal panel 18 this allows the horizontal panel 18 to be connected to the outside 13 portion of the elongated straps 15 connected to the complementary detachable fastening means 9 attached to the outside portion 13 of the front portion 6. Since the embodiment illustrated in FIG. 4 does not include the additional detachable fastening means 24 on the inside 11 portion of a horizontal panel 18, it is believed to have more flexibility than the embodiment of FIG. 5, and depending upon the needs of the individual wearer, will allow more upward body movement.

Additionally, FIGS. 1 and 3 illustrate an optional security straps 28 attached to the outer portion of the lateral horizontal panels 18. The security straps 28 each have a fastener means that connects to the fastener means on the opposing security strap attached to the opposing lateral horizontal panel 18. Examples of a fastener means 30 and 31 attached to the ends of the security straps 28 are hook and pile Velcro® type fasteners or male and female spring loaded fasteners.

Figure 6:
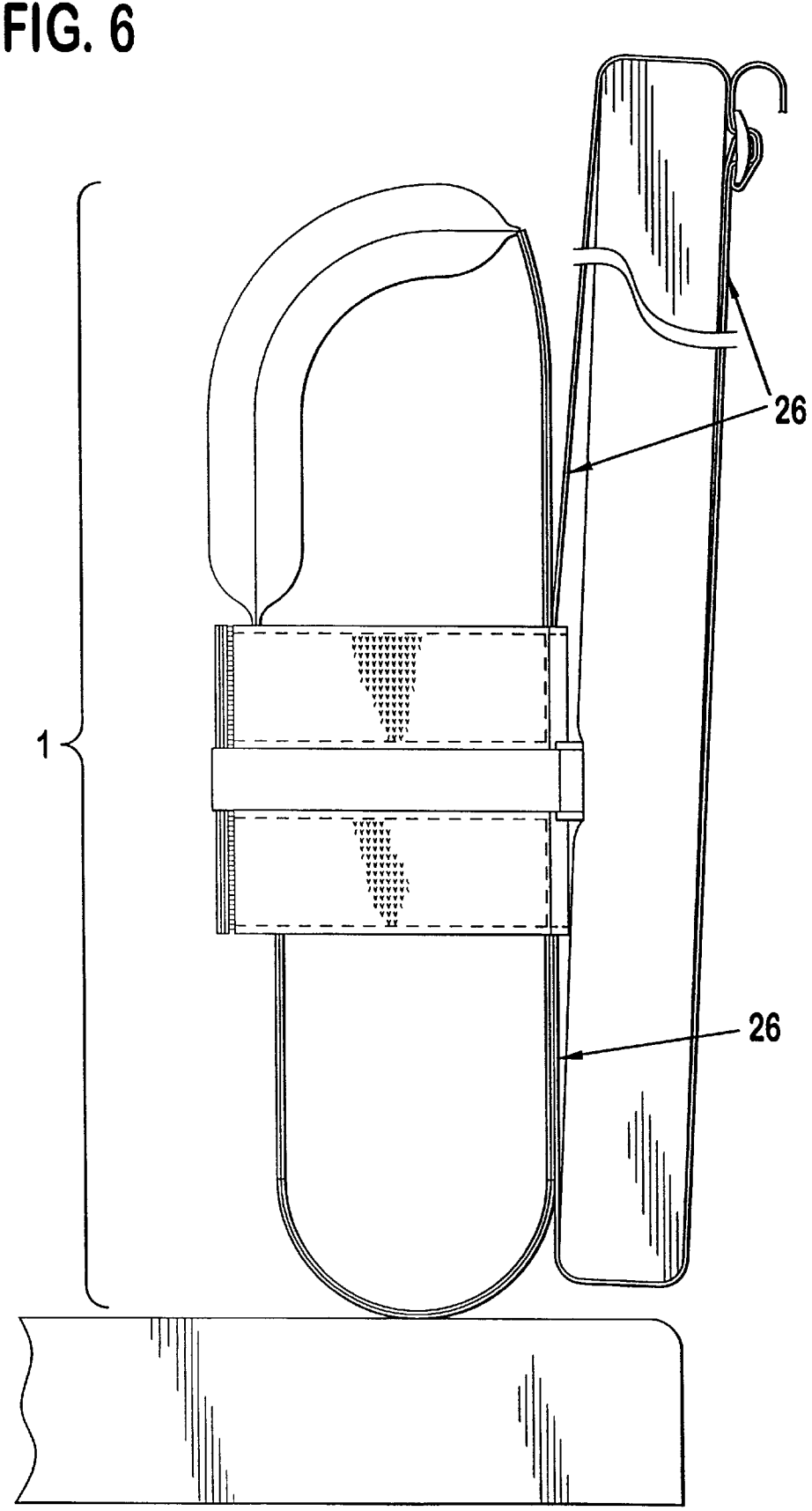
FIG. 6 is a side elevation depicting the personal restraint device of FIG. 1 on a bench type seat.

FIG. 6 shows a side elevational view of the personal restraint device 1 mounted to the back of an existing seat by means 26 for securing the personal restraint device 1 to the existing seat. Such seat securing means 26 include, but is not limited to, a vertical strap.

Figure 7:
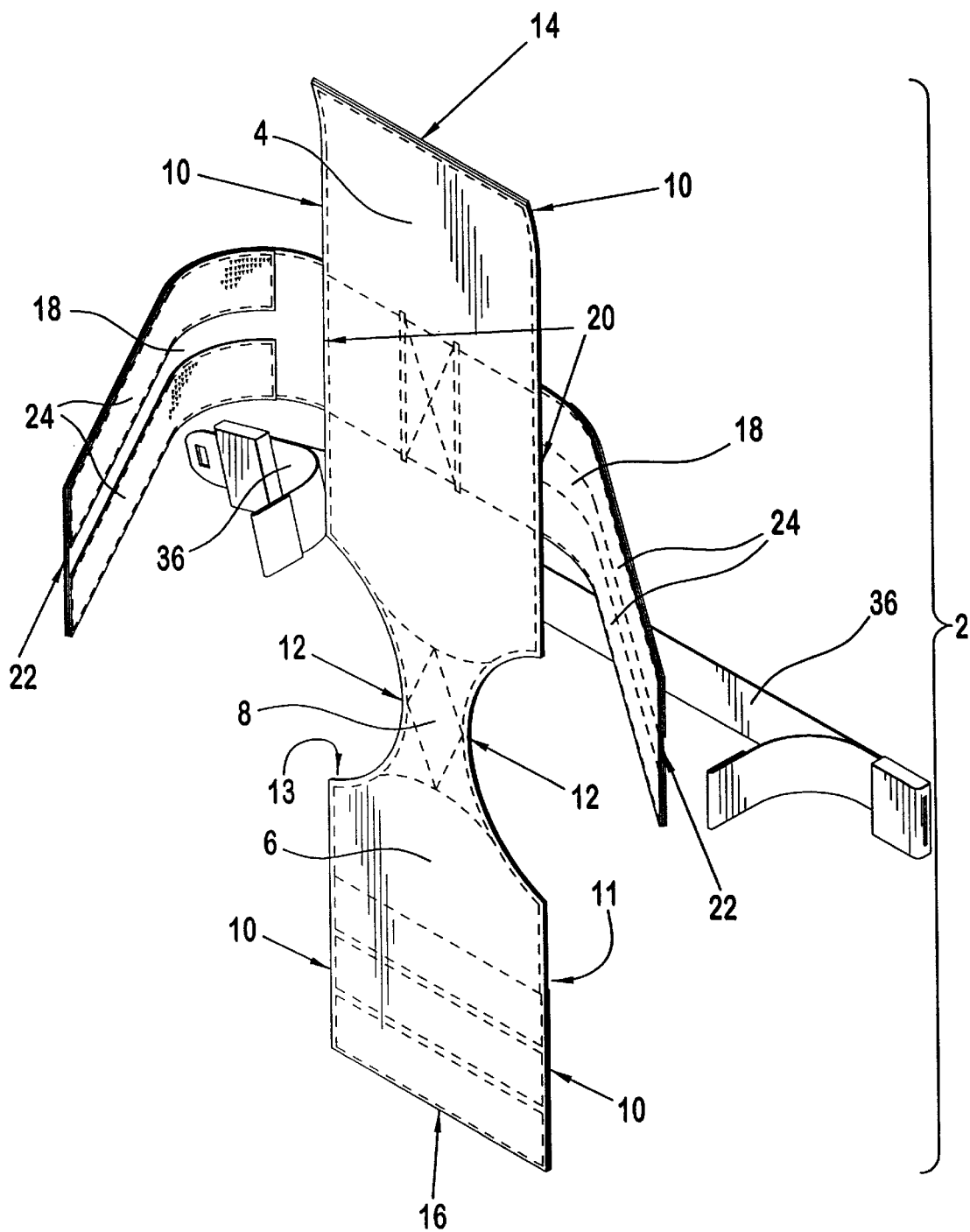
FIG. 7 is a perspective view of an alternative embodiment of the personal restraint device in accordance with the present invention.

In accordance with another embodiment of the present invention, FIG. 7 illustrates the personal restraint device having a planar body 2 with inside and outside portions, 11 and 13. The back and front portions, 4 and 6, are separated by a connector portion 8. The back and front portions, 4 and 6, have generally linear edges 10 and the connector portion 8 has concave lateral edges 12. The top and bottom transverse edges, 14 and 16, of the planar body 2 are generally linear. The back portion 4 has horizonal panels 18, each panel 18 having an end 20 connected to the back portion 4 of the planar body 2. Each horizonal strap 18 has a free end 22 which includes detachable fastening means either on the inside 11 or outside 13 of the horizontal panels 18 for securing the free ends 22 of the horizontal panel 18 to each other and the front portion 6 of the planar body 2. Examples of detachable fastening means would be a Velcro® type hook and pile fastener, a snap, or a zipper. The back portion 4 of the personal restraint device has means 36 for securing the personal restraint device to an existing seat.

FIG. 8 illustrates complete assembly of the personal restraint device illustrated in FIG. 7, whereby a person to be restrained can be seated on the connector portion 8 facing away from the back portion 4 and the front portion 6 is brought up against the person's body so that the front portion 6 is opposite the back portion 4 and the free ends 22 of the horizontal panels 18 are secured to the front portion 6 to define the parameter of the central portion.

Materials used to construct the personal restraint device can be selected from a wide variety of natural or synthetic materials such as duck cloth, vinyl and leather.

What is claimed is:

1. A personal restraint device that restrains a wearer on an existing seat structure comprising:

a elongated, generally planar body having back and front portions separated by a connector portion, the front and back portions have generally linear lateral edges and the connector portion has concave lateral edges, the top and bottom transverse edges of the planar body are generally linear;

at least two spaced apart straps, each strap having an end connected to only the top transverse edge and a free end that extends only frontally over the wearer and, each free end further includes a detachable fastener element that mates with the front portion;

a second, complementing detachable fastener element attached adjacent to the bottom transverse edge of the front portion and configured to be engageable with the detachable fastener element of the free end of the strap when the bottom transverse edge of the front portion is brought up in front of the wearer; and seat securing strap in back of and connected with the generally planar body for securing the personal restraint device to the existing seat structure without passing over the wearer.

2. The personal restraint device of claim 1 wherein the seat securing strap is vertical.

3. The personal restraint device of claim 1 wherein the seat securing strap is horizontal.

4. A personal restraint device that restrains a wearer on an existing seat structure comprising:

a longitudinal, generally planar body having back and front portions separated by a connector portion, the front and back portions have generally linear lateral edges and the connector portion has concave edges, the top and bottom transverse edges of the planar body are generally linear;

at least two horizontal panels, each panel having an end connected to the back portion of the planar body and a free end, each free end further including an element of a detachable fastening means;

a means for securing the free ends of the horizontal panels to the front portion of the planar body; and seat securing strap in back of and connected with the generally planar body for securing the personal restraint device to the existing seat structure without passing over the wearer.

5. The personal restraint device of claim 4 wherein the seat securing strap is vertical.

6. The personal restraint device of claim 4 wherein the seat securing strap is horizontal.

* * * * *